(12) United States Patent
Boone et al.

(10) Patent No.: US 8,370,734 B2
(45) Date of Patent: Feb. 5, 2013

(54) METHOD, SYSTEM AND APPARATUS FOR DATA REUSE

(75) Inventors: Keith W. Boone, Randolph, MA (US); Sunitha Chaparala, South Weymouth, MA (US); Cameron Fordyce, Providence, RI (US); Sean Gervais, Dorchester, MA (US); Roubik Manoukian, Belmont, MA (US); Harry J. Ogrinc, Medfield, MA (US); Robert G. Titemore, Lexington, MA (US); Jeffrey G. Hopkins, Lincoln, RI (US)

(73) Assignee: Dictaphone Corporation., Stratford, CT (US)

( * ) Notice: Subject to any disclaimer, the term of this patent is extended or adjusted under 35 U.S.C. 154(b) by 1123 days.

(21) Appl. No.: 11/545,414

(22) Filed: Oct. 10, 2006

(65) Prior Publication Data
US 2007/0038611 A1    Feb. 15, 2007

Related U.S. Application Data

(62) Division of application No. 10/448,320, filed on May 30, 2003.

(51) Int. Cl.
*G06F 17/00*    (2006.01)

(52) U.S. Cl. ........ 715/234; 715/235; 715/236; 715/760; 707/723; 707/737

(58) Field of Classification Search .......................... None
See application file for complete search history.

(56) References Cited

U.S. PATENT DOCUMENTS

| | | | |
|---|---|---|---|
| 4,477,698 A | 10/1984 | Szlam et al. | |
| 4,965,763 A | 10/1990 | Zamora | |
| 5,079,700 A * | 1/1992 | Kozoll et al. | 715/207 |
| 5,253,164 A | 10/1993 | Holloway et al. | |
| 5,325,293 A | 6/1994 | Dorne | |
| 5,327,341 A | 7/1994 | Whalen et al. | |
| 5,392,209 A | 2/1995 | Eason et al. | |
| 5,544,360 A | 8/1996 | Lewak et al. | |
| 5,664,109 A | 9/1997 | Johnson et al. | |
| 5,675,788 A * | 10/1997 | Husick et al. | 707/104.1 |
| 5,799,268 A | 8/1998 | Boguraev | |
| 5,809,476 A | 9/1998 | Ryan | |

(Continued)

FOREIGN PATENT DOCUMENTS

| | | |
|---|---|---|
| EP | 0584454 A1 | 3/1994 |
| WO | WO 9530201 A1 | 11/1995 |

OTHER PUBLICATIONS

U.S. Appl. No. 11/068,493, filed Feb. 28, 2005, Carus et al.

(Continued)

*Primary Examiner* — Farhan Syed
(74) *Attorney, Agent, or Firm* — Wolf, Greenfield & Sacks, P.C.

(57) ABSTRACT

A system and method may be disclosed for facilitating the creation or modification of a document by providing a mechanism for locating relevant data from external sources and organizing and incorporating some or all of said data into the document. In the method for reusing data, there may be a set of documents that may be queried, where each document may be divided into a plurality of sections. A plurality of section text groups may be formed based on the set of documents, where each section text group may be associated with a respective section from the plurality of sections and each section group includes a plurality of items. Each item may be associated with a respective section from each document of the set of documents. A selected item within a selected section text group may be focused. The selected item may be extracted to a current document. The current document may be exported to a host application.

8 Claims, 13 Drawing Sheets

U.S. PATENT DOCUMENTS

| | | | |
|---|---|---|---|
| 5,832,450 | A | 11/1998 | Myers et al. |
| 5,873,080 | A * | 2/1999 | Coden et al. .......................... 1/1 |
| 5,893,109 | A | 4/1999 | DeRose et al. |
| 5,970,463 | A | 10/1999 | Cave et al. |
| 5,974,412 | A | 10/1999 | Hazlehurst et al. |
| 6,006,221 | A | 12/1999 | Liddy et al. |
| 6,014,663 | A | 1/2000 | Rivette et al. |
| 6,021,202 | A | 2/2000 | Anderson et al. |
| 6,052,693 | A | 4/2000 | Smith et al. |
| 6,055,494 | A | 4/2000 | Friedman |
| 6,088,437 | A | 7/2000 | Amick |
| 6,182,029 | B1 | 1/2001 | Friedman |
| 6,192,112 | B1 | 2/2001 | Rapaport et al. |
| 6,289,353 | B1 | 9/2001 | Hazlehurst et al. |
| 6,292,771 | B1 | 9/2001 | Haug et al. |
| 6,347,329 | B1 | 2/2002 | Evans |
| 6,360,215 | B1 | 3/2002 | Judd et al. |
| 6,405,165 | B1 | 6/2002 | Blum et al. |
| 6,434,547 | B1 | 8/2002 | Mishelevich et al. |
| 6,438,533 | B1 | 8/2002 | Spackman et al. |
| 6,553,385 | B2 | 4/2003 | Johnson et al. |
| 6,684,188 | B1 | 1/2004 | Mitchell et al. |
| 6,810,410 | B1 | 10/2004 | Durham |
| 6,854,086 | B2 | 2/2005 | Umen et al. |
| 6,915,254 | B1 * | 7/2005 | Heinze et al. ...................... 704/9 |
| 6,947,936 | B1 | 9/2005 | Suermondt et al. |
| 6,978,275 | B2 * | 12/2005 | Castellanos et al. .......... 707/102 |
| 7,124,144 | B2 | 10/2006 | Christianson et al. |
| 7,287,031 | B1 * | 10/2007 | Karpf et al. ........................... 1/1 |
| 7,315,811 | B2 | 1/2008 | Cote et al. |
| 7,379,946 | B2 | 5/2008 | Carus et al. |
| 7,542,909 | B2 | 6/2009 | Cote et al. |
| 7,653,634 | B2 * | 1/2010 | Mathur .................... 707/999.01 |
| 7,774,196 | B2 | 8/2010 | Cote et al. |
| 7,783,474 | B2 | 8/2010 | Cote et al. |
| 2002/0007285 | A1 | 1/2002 | Rappaport |
| 2002/0095313 | A1 | 7/2002 | Haq |
| 2002/0143824 | A1 | 10/2002 | Lee et al. |
| 2002/0169764 | A1 | 11/2002 | Kincaid et al. |
| 2003/0046264 | A1 | 3/2003 | Kauffman |
| 2003/0061201 | A1 | 3/2003 | Grefenstette et al. |
| 2003/0079186 | A1 | 4/2003 | Gondo et al. |
| 2003/0115080 | A1 | 6/2003 | Kasravi et al. |
| 2003/0154080 | A1 | 8/2003 | Godsey et al. |
| 2003/0208382 | A1 | 11/2003 | Westfall |
| 2003/0233345 | A1 | 12/2003 | Perisic et al. |
| 2004/0103075 | A1 | 5/2004 | Kim et al. |
| 2004/0139400 | A1 * | 7/2004 | Allam et al. ................. 715/526 |
| 2004/0186746 | A1 | 9/2004 | Angst et al. |
| 2004/0205638 | A1 | 10/2004 | Thomas et al. |
| 2004/0220895 | A1 | 11/2004 | Carus et al. |
| 2004/0243545 | A1 | 12/2004 | Boone et al. |
| 2004/0243551 | A1 | 12/2004 | Boone et al. |
| 2004/0243552 | A1 | 12/2004 | Titemore et al. |
| 2004/0243614 | A1 | 12/2004 | Boone et al. |
| 2005/0108010 | A1 | 5/2005 | Frankel et al. |
| 2005/0114122 | A1 | 5/2005 | Uhrbach et al. |
| 2005/0120020 | A1 | 6/2005 | Carus et al. |
| 2005/0120300 | A1 | 6/2005 | Schwager et al. |
| 2005/0144184 | A1 | 6/2005 | Carus et al. |
| 2005/0192792 | A1 | 9/2005 | Carus et al. |

OTHER PUBLICATIONS

U.S. Appl. No. 10/953,471, filed Feb. 29, 2004, Cote et al.
U.S. Appl. No. 11/007,626, filed Dec. 4, 2004, Cote et al.
U.S. Appl. No. 10/840,428, filed May 7, 2004, Carus et al.
U.S. Appl. No. 10/951,281, filed Sep. 27, 2004, Cote et al.
U.S. Appl. No. 11/069,203, filed Feb. 28, 2005, Cote et al.
U.S. Appl. No. 10/953,448, filed Sep. 30, 2004, Carus.
U.S. Appl. No. 10/951,291, filec Sep. 27, 2004, Uhrbach.
U.S. Appl. No. 10/953,474, filed Sep. 29, 2004, Frankel.
U.S. Appl. No. 11/007,626, filed Dec. 8, 2004, Cote.
U.S. Appl. No. 10/787,889, filed Feb. 27, 2004, Carus.
U.S. Appl. No. 10/948,625, filed Sep. 23, 2004, Schwager.
U.S. Appl. No. 10/840,428, filed May 7, 2004, Carus.
U.S. Appl. No. 10/447,290, filed May 29, 2003, Boone.
U.S. Appl. No. 10/448,320, filed May 30, 2003, Boone.
U.S. Appl. No. 10/448,317, filed May 30, 2002, Boone.
U.S. Appl. No. 10/448,325, filed May 30, 2003, Titemore.
U.S. Appl. No. 10/413,405, filed Apr. 15, 2003, Carus.
McGregor, C. et al. "The e-baby data warehouse: a case study" System Sciences, 2002, HICSS, Proceedings of the 35th Hawaii International Conference on Systems Sciences, Jan. 7-10, 2001, Piscataway, NJ, US, IEEE, Los Alamitos, CA, USA, Jan. 7, 2001, pp. 2871-2877.
Extended European Search Report from European Application 06786051 dated Jul. 8, 2010.
Examination Report and Supplementary European Search Report from European Application EP04753663, dated Dec. 20, 2007.
Smith et al., "MICROARRAS: An Advanced Full-Text Retrieval and Analysis System," ACM 1987, p. 187-195.
Fei Song et al., A Graphical Interface to a Semantic Medical Information System, Journal of Foundations of Computing and Decision Sciences, 22(2), 1997.
Fei Song, et al., A Cognitive Model for the Implementation of Medical Problem Lists, Proc. of the First Congress on Computational Medicine, Public Health and Biotechnology, Austin, TX, 1994.
Fei Song, et al., A Graphical Interface to a Semantic Medical Information System, Karp-95 Proc. of the Second International Symposium on Knowledge Acquisition, Representation and Processing, pp. 107-109, 1995.
Epic Web Training Manual, EpicWeb pp. 1-33, downloaded May 2, 2002.
B. Hieb, Research Note, NLP Basics for Healthcare, Gartner Research, Aug. 16, 2002.
C. Shalizi et al., Pattern Discovery in Time Series, Part I: Theory, Algorithm, Analysis and Convergence, J. of Machine Learning Research, (2002), Submitted Oct. 28, 2002, published 2002.
C. Nevill-Manning et al., The Development of Holte's 1R Classifier, Dept. of Computer Science, University of Waikato, New Zealand, undated.
Cutting et al., A Practical Part-of-Speech Tagger, Xerox Palo Alto Research Center, undated.
Zavrel et al., Recent Advances in Memory-Based Part-of-Speech Tagging, ILK/Computational Linguistics, Tilburg University, The Netherlands, undated.
Brill, Some Advances in Transformation-Based Part of Speech Tagging, Spoken Language Systems Group, Massachusetts Institute of Technology, undated.
Nivre, DAC723: Language Technology Finite State Morphology, Vaxjo University of Mathematics and Systems Engineering, p. 1/11, undated.
Creutz, Morphology and Finite-State Transducers, Oct. 31, 2001, Chap. 3, Jurafsky & Martin.
http://www.comp.lancs.ac.uk/computing/research/stemming/general/index.htm downloaded Jul. 19, 2004.
http://www.comp.lancs.ac.uk/computing/research/stemming/general/stemmingerrors.htm downloaded Jul. 19, 2004.
http://www.comp.lancs.ac.uk/computing/research/stemming/general/performance.htm, downloaded Jul. 19, 2004.
Lee et al., Cleansing Data for Mining and Warehousing, Lecture Notes in Computer Science vol. 1677 archive, Proc. of the 10th International Conference on Database and Expert Systems Applications, pp. 751-760, Springer-Verlag, London 1999.
Van Rijsbergen, Search Strategies Information Retrieval, 2nd Ed., Ch. 5, Butterworths, London 1979.
Day, Extracting Knowledge from Text Using Learning by Constraint Relaxation (LCR), CSI, Florida Institute of Technology, www.csi-inc.com/CSI/pdf.jday_icim02.pdf, undated.
Gale et al., Discrimination Decisions for 100,000-Dimensional Spaces, Current Issues in Computations Linguistics, pp. 429-450, Kluwer Academic Publishers, 1994.
Daelemans et al. TiMBL: Tilburg Memory Based Learner, version 4.3 Reference Guide, ILK Research Group Technical Report Series No. 04-02 (ILK-0402), ILK Research Group, Tilburg University, Tilburg, Netherlands, Nov. 6, 2002.
Case Study: Massachusetts Medical Society, http://www.microsoft.com/resources/casestudies/CaseStudy.asp?CaseStudyID=14931 , Jan. 13, 2004.

Braithwaite, Continuity of Care Record (CCR) HL7 Board of Directors, http://www.hl7.org/library/himss/2004Orlando/ContinuityofCareRecord.pdf, undated.

Waegemann, EHR vs. CCR: What is the difference between the electronic health record and the continuity of care record?, Medical Records Institute, 2004.

Press Release: Kryptiq Announces Support of CCR Initiative and Introduces New Solutions that Enable Information Portability, Accessibility and Clinical system Interoperability. http://www.kryptiq.com/News/PressReleases/27.html , downloaded Feb. 17, 2004.

Work Item Summary: WK4363 Standard Specification for the Continuity of Care Record (CCR), http://www.astm.org/cgi-bin/SoftCart.exe/DATABASE.CART/WORKITEMS/WK4363.htm?E+mystore, Mar. 3, 2004.

Continuity of Care Record (CCR): The Concept Paper of the CCR, v. 2.1b, http://www.bhtinfo.com/CCR.Concept%20Paper.1.5.doc.

Continuity of Care Record (CCR), AAFP Center for Health Information Technology, http://www.centerforhit.org/x201.xml, posted Aug. 20, 2004.

Core Measures web page, Joint Commission on Accreditation of Healthcare Organizations, http://www.jcaho.org/pms/core+measures/, downloaded Mar. 22, 2004.

Specifications Manual for National Implementation of Hospital Core Measures, v. 2.0, Joint Commission on Accreditation of Healthcare Organizations, http://www.jcaho.org/pms/core+measures/information+on+final+specifications.htm.

Code Information and Education web page, American Medical Association, http://www.ama-assn.org/ama/pub/category/3884.html, printed Mar. 22, 2004.

Yang et al. Faster algorithm of string comparison, Pattern Analysis and Applications, v. 6, No. 1, Apr. 2003: pp. 122-133.

Hardware Reference Manual, Release 3 for DOS, revised Jan. 1994, PIKA Technologies, Inc., Ontario, Canada, available at http://www.piketechnologies.com/downloads/legac/AVA%20B-Series%20Hardware%20Manual.pdf, last accessed Jul. 25, 2005.

Customizing D/41 Call Analysis, date unknown, Intel Corp., Santa Clara, California, available at http://resource.intel.com/telecom/support/appnotes/custd41d.htm, last accessed Jul. 25, 2005.

Fei Song, et al., A Graphical Interface to a Semantic Medical Information System, Journal of Foundations of Computing and Decision Sciences, 22(2), 1997.

Fei Song, et al., A Cognitive Model for the Implementation of Medical Problem Lists, Proceedings of the First congress on Computational medicine, Public health and Biotechnology, Austin, Texas, 1994.

Fei Song, et al., A Graphical Interface to a Semantic medical Information System, Karp—95, Proceedings of the Second International Symposium on Knowledge Acquisition, Representation and Processing, pp. 107-109, 1995.

Epic Web Training manual, pp. 1-33, 2002.

B. Heib, Research Note, NLP Basics for healthcare, Aug. 16, 2002.

C. Shalizi et al., Pattern Discovery in Time Series, Part I: Theory, Algorithm, Analysis, and Convergence, Journal of Machine Leaning Research? (2002) ?-? Submitted Oct. 28, 2002; Published ?/2002.

C. Nevill-Manning et al., The Development of Holte's 1R Classifier, Department of Computer Science.

D. Cutting et al., A Practical Part-of-Speech Tagger, Xerox Palo Alto Research Center.

J. Zavrel, et al., Recent advances in memory-Based Part-of-Speech Tagging, ILK/Computational Linguistics.

E. Brill, Some Advances in Transformation-Based Part of Speech Tagging, Spoken Language Systems Group.

J. Nivre, DAC723: Language Technology Finite State Morphology, Vaxjo University of Mathematics and Systems Engineering, p. 1/11.

M. Creutz, Morphology and Finite-State Transducers, Oct. 31, 2001, Chapter 3, Jurafsky & Martin.

http://www.comp.lancs.ac.uk/computing/research/stemming/general/index.htm, printed Jul. 19, 2004.

http://www.comp.lancs.ac.uk/computing/research/stemming/general/stemmingerrors.htm, printed Jul. 19, 2004.

http://www.comp.lancs.ac.uk/computing/research/stemming/general/performance.htm, printed Jul. 19, 2004.

M. Lee et al., Cleansing Data for Mining and Warehousing, Lecture Notes in Computer Science vol. 1677 archive, Proceedings of the 10$^{th}$ International Conference on Database and Expert Systems Applications, pp. 751-760, Springer-Verlag, London 1999.

C. Van Rijsbergen, Information Retrieval, 2$^{nd}$ Ed., Ch. 5, Butterworths, London, 1979.

J. Day, Extracting Knowledge from Text Using Learning by Constraint Relaxation (LCR), CSI, www.csi-inc.com/CSI/pdf/jday_icim02.pdf.

W. Gale et al., Discrimination Decisions for 100,000-Dimensional Spaces, Current Issues in Computational Linguistics, pp. 429-450, Kluwer Academic publishers, 1994.

W. Daelemans et al., TiMBL: Tilbury Memory Based Learner, version 5.0, Reference Guide, ILK Research Group Technical Report Series No. 04-02 (ILK-0402), ILK Research Group, Tilburg University, Tilburg, Netherlands, 2004.

Case Study: Massachusetts medical Society http://www.microsoft.com/resources/casestudies/CaseStudy.asp?CaseStudyID=14931 posted Jan. 13, 2004.

W. Braithwaite, Continuity of Care Record (CCR) http://www.h17.orp/library/himss/2004Orlando/ContinuityofCareRecord.pdf.

C. Waegemann, EHR vs. CCR: What is the difference between the electronic health record and the continuity of care record?, Medical Records Institute, 2004.

Press Release: Kryptiq Announces Support of CCR Initiative and Introduces new Solutions that Enable Information Portability, Accessibility and Clinical System Interoperability, http://www.kryptig.com/News/PressReleases/27.html, posted Feb. 17, 2004.

Work Item Summary: WK4363 Standard Specification for the Continuity of Care Record (CCR), http://www.astm.org/cgi-bin/SoftCart.exe/DATABASE.CART/WORKITEMS/WK4363.htm?E+mystore Mar. 3, 2004.

Continuity of Care Record (CCR): The concept Paper of the CCR, v. 2.1b, http://www.bhtinfo.com/CCR.Concept%20Paper.1.5.doc.

Continuity of Care Record, American Academy of Family Physicians, http://www.aafp.org/x24962.xml?printxml posted Nov. 12, 2003.

Continuity of Care Record (CCR), AAFP Center for Health Information Technology, http://www.centerforhit.org/x201.xml posted Aug. 20, 2004.

Core Measures web page, Joint commission on Accreditation of Healthcare Organizations, http://www.jcaho.org/pms/core+measures/ printed Mar. 22, 2004.

Specifications Manual for National Implementation of Hospital Core Measures, v. 2.0, Joint Commission on Accreditation of Healthcare Organizations, http://www.icaho.org/pms/core+measures/information+on+final+specifications.htm.

Code Information and Education web page, American medical Association, http://www.ama-assn.org/ama/pub/category/3884.html printed Mar. 22, 2004.

Category III CPT Codes, American Medical Association, http://www.ama-assn.org/ama/pub/article/3885-4897.html printed Mar. 22, 2004.

ICD-9-CM Preface (FY04), http://ftp.cdc.gov/pub/Health_Statistics/NCHS/Publications/ICD9-CM/2004/Prefac05.rtf.

ICD-9-CM Official Guidelines for Coding and Reporting, effective Oct. 1, 2003.

Q. X. Yang, et al., "Faster algorithm of string comparison," Pattern Analysis and Applications, vol. 6, No. 1, Apr. 2003: pp. 122-133.

Hardware Reference Manual, Release 3 for DOS, revised Jan. 1994, PIKA Technologies, Inc., Ontario, Canada, available at http://www.pikatechnologies.com/downloads/legacy/AVA%20B-Series%20Hardware%20Manual.pdf (last accessed Jul. 25, 2005).

Customizing D/41 Call Analysis, date unknown, Intel Corp., Santa Clara, California, available at http://resource.intel.com/telecom/support/appnotes/custd41d.htm (last accessed Jul. 25, 2005).

* cited by examiner

FIG. 4

METHOD, SYSTEM AND APPARATUS FOR DATA REUSE

CROSS-REFERENCE TO RELATED APPLICATIONS

This is a divisional application of U.S. Ser. No. 10/448,320, filed May 30, 2003, which relates to U.S. patent application Ser. No. 10/413,405, filed Apr. 15, 2003, U.S. patent application Ser. No. 10/447,290, filed on May 29, 2003; U.S. patent application Ser. No. 10/448,317, filed on May 30, 2003; and U.S. patent application Ser. No. 10/448,325, filed on May 30, 2003. The disclosure of each such application is hereby incorporated by reference in its entirety where appropriate for teachings of additional or alternative details, features, and/or technical background, and priority is asserted from each.

BACKGROUND OF THE INVENTION

It may be generally known that various governmental agencies, businesses, health care institutions or other similar entities generate many reports. For example, a metropolitan police department may generate arrest reports for the people arrested by the members of the police department. In the medical industry, physicians, nurses and health care administrators generate voluminous patient records.

Often, the reports generated by these entities contain similar text. For example, a report generated by a police officer for a repeat offender may contain the same information with respect to address, history, etc. Another example may be reports generated by a primary care doctor and a referred specialist, which may contain the same information with regard to the reported health problem, health history, etc.

Conventional report generating systems may allow a user to reuse text contained in a previous report and apply that text to a current report. For example, a user may search a document library for the previous report and then 'cut-and-paste' the relevant sections from the previous report to the current report.

However, these conventional report generating systems have their drawbacks and disadvantages. For example, such typical report generating systems do not provide for a convenient method of focused searching of previous reports. Another drawback may be that the conventional systems do not organize information contained within multiple previous reports in a document library. Yet another drawback may be that conventional systems do not offer a mechanism to quickly add reusable material to a document.

SUMMARY OF THE INVENTION

An advantage exists in the present invention which facilitates the creation or modification of a document by providing a mechanism for locating relevant data from external sources and organizing and incorporating some or all of the data into the document.

Another advantage of the present invention includes facilitating the dictation of documents by providing a selection of data elements and/or text sections that have been automatically extracted from other documents that are likely to be relevant to the type of document being dictated. The present invention may allow a user to select which data elements and/or text sections are to be reused and where in the new document they should be inserted, automatically populating the new document with the data and text sections. An advantage exists in that valuable time may be saved when creating these new documents, and the present invention may be especially effective when substantial portions of the content of a new dictation is essentially a repeat of what has been stated before in previous dictations. An additional benefit of the present invention is that new dictations will likely be more complete, as importing data elements and text sections will prompt a user to highlight certain key information, which can lead to higher consistency and efficiency in future dictations. Another benefit may be access to data and/or text sections previously dictated by other third party users, which otherwise may not have been accessible.

As such, in a first aspect, the present invention includes an embodiment that relates to a method of reusing data. The method includes querying for a set of documents, where each document may be divided into a plurality of sections. The method also includes forming a plurality of section text groups based on the set of documents, where each section text group may be associated with a respective section from the plurality of sections and each section group includes a plurality of items. Each item may be associated with a respective section from each document of the set of documents. The method further includes focusing on a selected item within a selected section text group and extracting the selected item to a working draft document. The method yet further includes exporting the working draft document to a host application.

In a second aspect, the present invention includes an embodiment that pertains to a system for reusing data. The system includes at least one processor, a memory coupled to the at least one processor, a document library configured to be stored in the memory, and a reuse client configured to be stored as a computer programmable readable media in the memory and to be executed by the at least one processor. The document library comprises documents, where each document may be divided into a plurality of sections. The reuse client may be configured to query for documents in the document library and to form a plurality of section text groups based on the documents. Each section text group may be associated with a respective section from the plurality of sections and each section group comprises a plurality of items, where each item may be associated with a respective section from each document of the documents.

In a third aspect, the present invention includes an embodiment that relates to an apparatus for reusing data. The apparatus includes a means for querying for a set of documents, where each document may be divided into a plurality of sections. The apparatus also includes a means for forming a plurality of section text groups based on the set of documents, where each section text group may be associated with a respective section from the plurality of sections and each section group comprises a plurality of items. Each item may be associated with a respective section from each document of the set of documents.

In a fourth aspect, the present invention includes an embodiment that pertains to a computer readable storage medium on which may be embedded one or more computer programs. The one or more computer programs implements a method of reusing data. The one or more computer programs includes a set of instructions for querying for documents in a document library, where each document may be divided into a plurality of sections. The one or more computer programs also includes forming a plurality of section text groups based on the set of documents, where each section text group may be associated with a respective section from the plurality of sections and each section group comprises a plurality of items. Each item may be associated with a respective section from each document of the set of documents.

The above advantages and features are of representative embodiments only, and are presented only to assist in understanding the invention. It should be understood that they are not to be considered limitations on the invention as defined by the claims, or limitations on equivalents to the claims. Additional features and advantages of the invention will become apparent from the drawings, the following description, and the claims.

BRIEF DESCRIPTION OF THE DRAWINGS

While the specification concludes with claims particularly pointing out and distinctly claiming the present invention, it may be believed the same will be better understood from the following description taken in conjunction with the accompanying drawings, which illustrate, in a non-limiting fashion, the best mode presently contemplated for carrying out the present invention, and in which like reference numerals designate like parts throughout the figures, wherein:

FIG. 4 illustrates a reuse viewer GUI provided by the reuse client module in accordance with yet another embodiment;

DETAILED DESCRIPTION OF THE EMBODIMENTS

For simplicity and illustrative purposes, the principles of the present invention are described by referring mainly to exemplary embodiments thereof. However, one of ordinary skill in the art would readily recognize that the same principles are equally applicable to, and can be implemented in, all types of network systems, and that any such variations do not depart from the true spirit and scope of the present invention. Moreover, in the following detailed description, references are made to the accompanying figures, which illustrate specific embodiments. Electrical, mechanical, logical and structural changes may be made to the embodiments without departing from the spirit and scope of the present invention. The following detailed description is, therefore, not to be taken in a limiting sense and the scope of the present invention is defined by the appended claims and their equivalents.

Embodiments of the present invention relate to data reuse. In particular, a reuse client module may be configured to provide to a user a reuse viewer graphical user interface (GUI) with a data filter component, a section viewer component, and a reuse draft component. The data filter component may be configured to provide the user the ability to search for a plurality of documents based on number of query parameters. In the set of retrieved documents, each document may be divided into sections and text may be associated with each section.

The reuse client module may be also configured to group together the text associated with the same section from each document in the set of documents. The reuse client module may be further configured to display the names of the plurality of the sections in a collapsed tree format in the section viewer component of the reuse viewer GUI. The reuse client module may also be further configured to display the associated text from each document when a section name may be expanded.

The reuse client may be further configured to display a draft document (or report) in the reuse draft component of the reuse viewer GUI, where the draft document displays the associated section names as displayed on the section viewer component. A user may hover over a section in the draft document and the selected section will highlight. The user may then select the corresponding section(s)/paragraph(s) in the section viewer component. The selected section(s)/paragraph(s) are then appended to the draft document. The reuse client module may be configured to send the draft document to a host application when the user may be finished.

Figure 1:
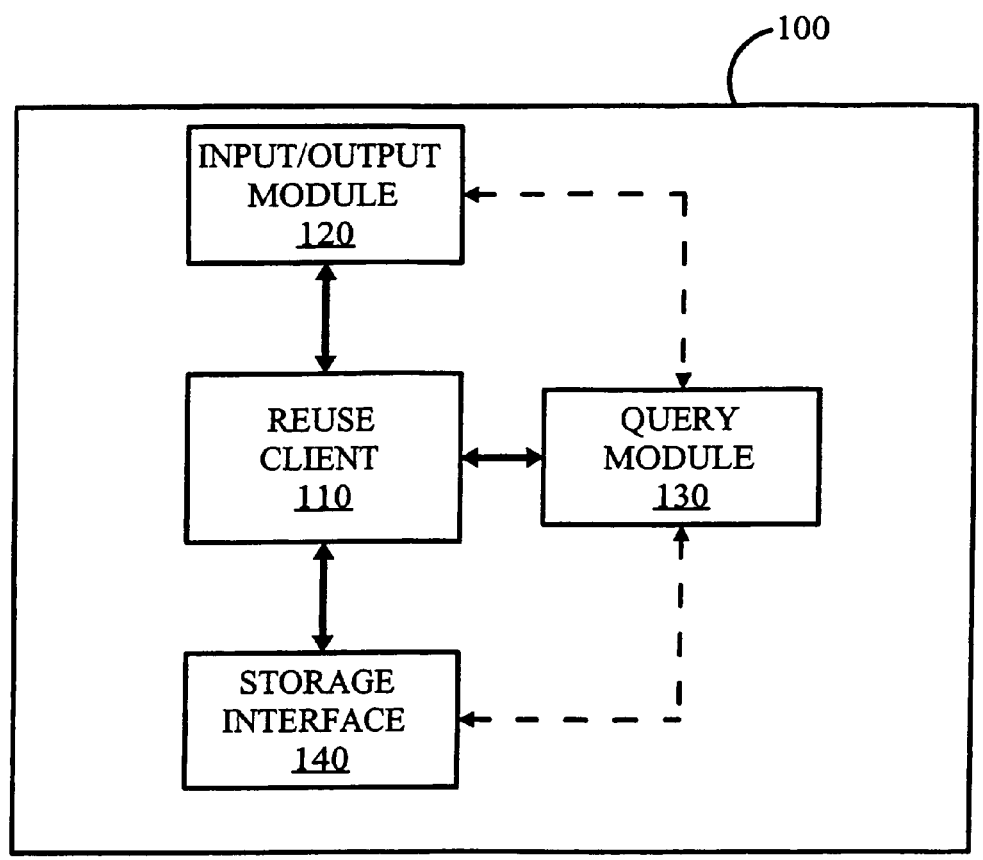
FIG. 1 illustrates an exemplary architecture of a reuse client module in accordance with an embodiment.

FIG. 1 illustrates an exemplary architecture of a reuse client module 100 in accordance with an embodiment. It should be readily apparent to those of ordinary skill in the art that the exemplary architecture depicted in FIG. 1 represents a generalized schematic illustration and that other components may be added or existing components may be removed or modified.

As shown in FIG. 1, the reuse client module 100 includes a reuse client 110, an input/output (I/O) module 120, a query module 130, and a storage interface 140. The reuse client 110 may be configured to provide the functionality for the reuse client module 100. For example, the reuse client 110 may be configured to perform actions in response to user input received through the I/O module 120. More specifically, the client reuse 110 may provide a user the capability to reuse data extracted from existing documents stored in a document library. The reuse client module 110 may present the extracted data in a manner that enables one to quickly incorporate the relevant extracted portions into a draft document.

The reuse client 110 may also be configured to interface with the 110 module 120. The 110 module 120 may be configured to provide a user interface for the user to utilize the reuse client module 110. More particularly, the reuse client 110 may invoke the I/O module 120 to provide an interface to query for document(s), to provide an interface to show extracted data from the found documents, and/or to provide an interface to show a draft document with extracted data selected for reuse. In other embodiments, the functionality of the I/O module 120 may be merged into the reuse client 110.

The reuse client 110 may be further configured to interface with the storage interface 140. The storage interface 140 may provide a mechanism for the reuse client module 100 to access existing documents for querying. The storage interface 140 may be a set of function calls, remote procedure calls or other similar interfaces.

The reuse client 110 may be further configured to interface with the query module 130. The query module 130 may receive query parameters from an interface generated by the I/O module 120 to search for a document or a set of documents. Alternatively, the query module 130 may receive the query parameters through the reuse client 110. The query module 130 may be configured to implement a search through either the storage interface 140 directly or through the reuse client 110 for the documents that match the received query parameters. For the matching documents, the query module may forward the matching documents to the reuse client 110. In other embodiments, the functionality of the query module 110 may be merged with the reuse client 110.

The reuse client module 100 may be implemented as a software program, a utility, a subroutine, or other similar programming entity. In this respect, the reuse client module 100 may be implemented using software languages such as C, C++, JAVA, etc. Alternatively, the reuse client module 100 may be implemented as an electronic device utilizing an application specific integrated circuit, discrete components, solid-state components or a combination thereof.

Figure 2:
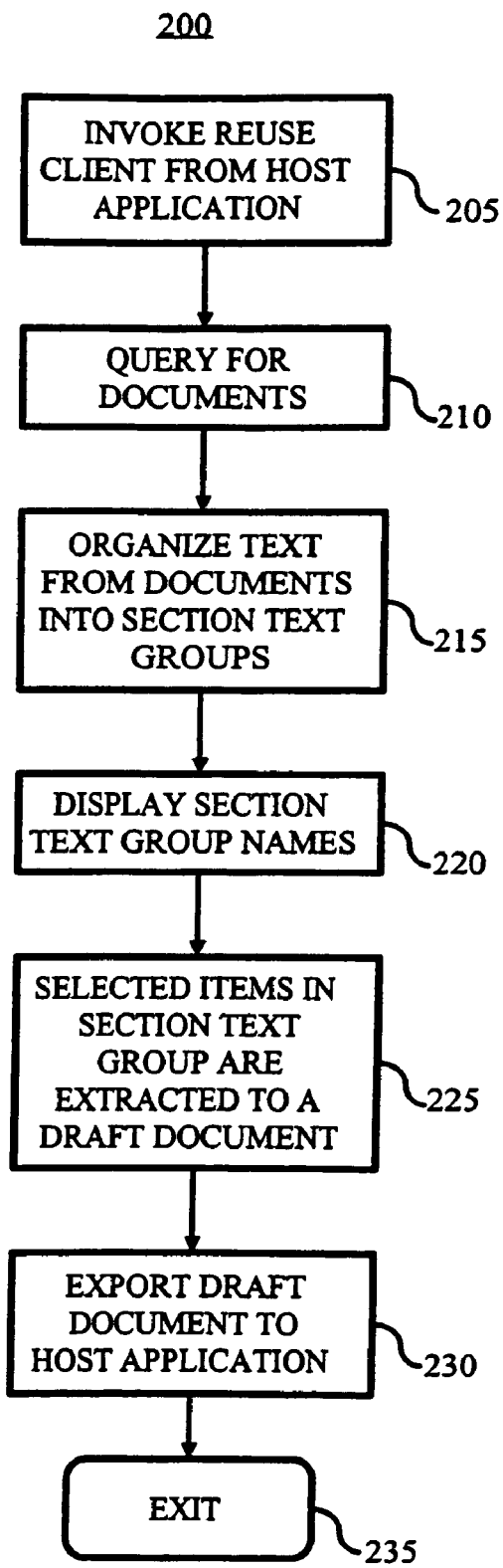
FIG. 2 illustrates an exemplary flow diagram for the reuse client in accordance with another embodiment.

FIG. 2 illustrates an exemplary flow diagram 200 for the reuse client 110 in accordance with another embodiment. It should be readily apparent to those of ordinary skill in the art that this method 200 represents a generalized illustration and that other steps may be added or existing steps may be removed or modified.

As shown in FIG. 2, a host application may invoke the reuse client module 100 by initiating a command, in step 205. Alternatively, the host application may have a menu item that represents the reuse client 100 or by a function call. Once invoked, the reuse client 110 may invoke the 110 module 120 to provide a graphical user interface for a user to input query parameters.

In step 210, the query module 130 may initiate a search for the requested documents based on the received query parameters. if matching documents are found, the query module 130 may forward the matching documents to the reuse client 110. Although not shown, if no matching documents are found, the query module 130 may notify the user of the lack of matching documents through the 110 module 120.

In step 215, the reuse client 110 may be configured to organize the retrieved document(s). More specifically, the documents are divided into a plurality of sections. The reuse client 110 may be configured to create a section group for each of the sections in the document. For each section, the reuse client may extract the text from the section from each of the documents and group the extracted text within the section group.

In step 220, the reuse client 110 may invoke the 110 module 120 to display the section groups in a collapsed tree format. The I/O module 120 may be configured to expand a section group in response to a user event. The I/O module 120 may then display the extracted text from the documents for the expanded section group.

In step 225, a user may select extracted text within an expanded section group. The reuse client 110 may then place the selected extracted text within a draft document provided by the I/O module 120.

In step 230, after completion of the selection extracted text, the reuse client 110 may export the draft document to the host application in response to another user event received through the 110 module 120. Subsequently, in step 235, the reuse client module 100 may exit.

Accordingly, a user may be presented with relevant document(s) for reuse through the reuse client module 110. Moreover, a user may quickly view relevant portions within the relevant document(s) to reuse in the user's current document.

Figure 3:
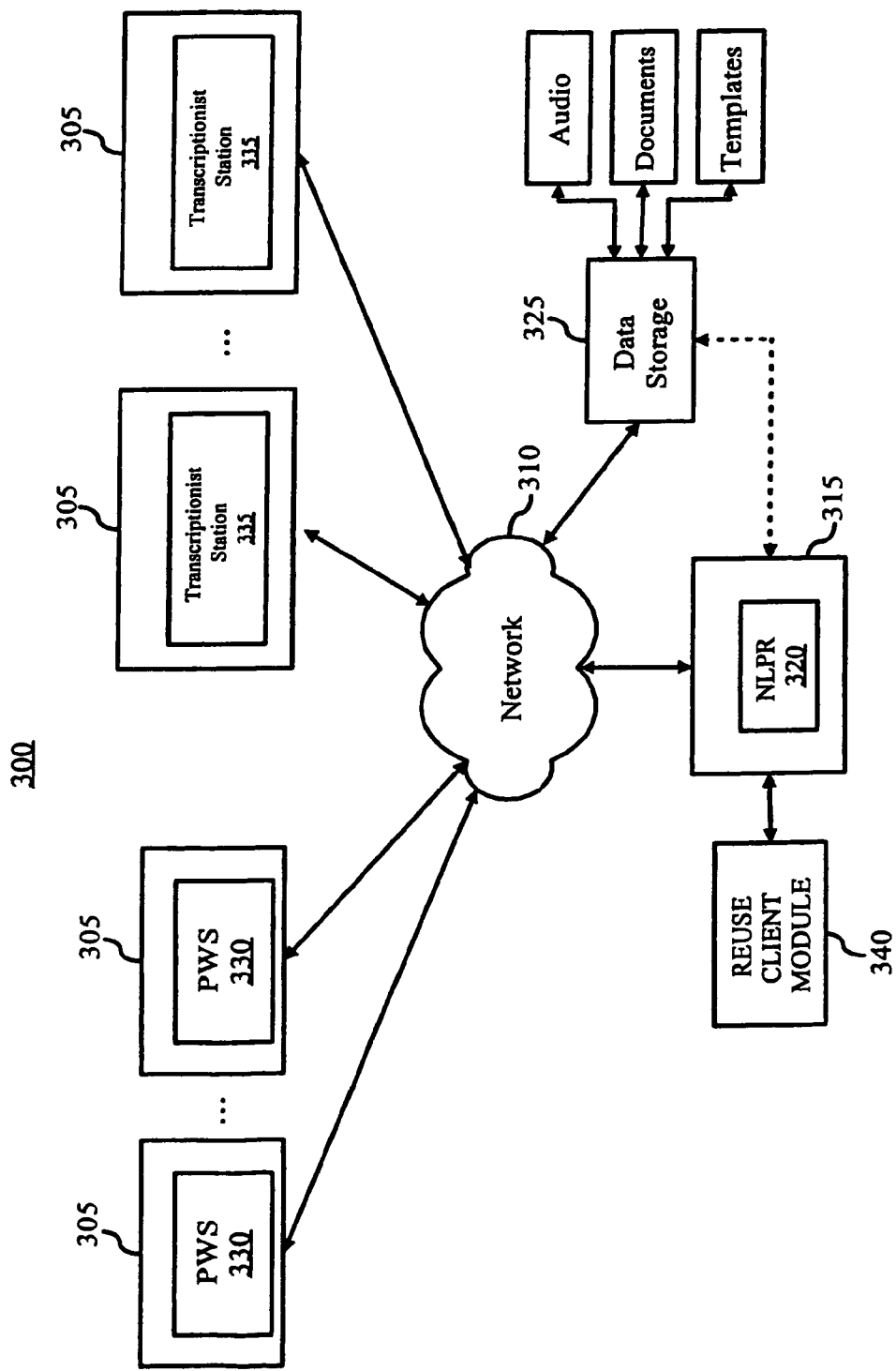
FIG. 3 illustrates a natural language patient record (NLPR) system utilizing a reuse client module in accordance with yet another embodiment.

FIG. 3 illustrates a natural language patient record (NLPR) system 300 utilizing a reuse client module in accordance with yet another embodiment. As shown in FIG. 3, the NLPR system 300 includes a plurality of workstations 305 interconnected by a network 310. The NLPR system 300 also includes a server 315 executing a computer readable version 320 of the NLPR system and data storage 325.

The workstations 305 may be personal computers, laptops, workstations, or other similar computing element. The workstations 305 execute a physician workstation (PWS) client 330 from the NLPR system 300. The PWS client 325 provide the capability for a physician to dictate, review, and/or edit medical records to the NLPR system 300.

The workstations 305 also execute a transcriptionist client 335 for a transcriptionist to access and convert audio files into electronic text. The NLPR system 300 may also use speech engines to automatically convert dictations from physicians into electronic text.

The network 310 may be configured to provide a communication channel between the workstations 305 and the server 315. The network 310 may be a wide area network, local area network or combination thereof. The network 310 may implement wired protocols (e.g., TCP/IP, X.25, IEEE802.3, IEEE802.5, etc.), wireless protocols (e.g., IEEE802.11, CDPD, etc.) or a combination thereof.

The server 315 may be a computing device capable of providing services to the workstations 305. The server 315 may be implemented using HP RX5670™, IBM xSeries205™, Sun Microsystem SunFire V1280™, or other similar computing platform. The server 315 may be configured to execute a computer readable version of the NLPR software 320. The NLPR software provides functionality for the NLPR system 300. The NLPR system 300 may receive audio files and/or documents by other network access means such as electronic mail, file transfer protocols, and other network transferring protocols.

The data storage 325 may be configured to interface with network 310 and provide storage services to the workstations 305 and the server 315. The data storage 325 may also be configured to store a variety of files such as audio, documents, and/or templates. In some embodiments, the data storage 325 includes a file manager (not shown) that provides services to manage and access the files stored therein. The data storage 325 may be implemented as a network-attached storage or through an interface through the server 315.

The server 315 may be further configured to interface with an embodiment of the reuse client module 340. A user may invoke the reuse client module 340 through a PWS client 320. For example, the reuse client module 340 may be a menu item on a graphical user interface of the PWS client 320. Alternatively, a user may use a command line prompt at the PWS client 320 to invoke the reuse client module. Once invoked, the reuse client module 340 may display a reuse viewer graphical user interface (GUI) as shown in FIG. 4.

Figure 4:
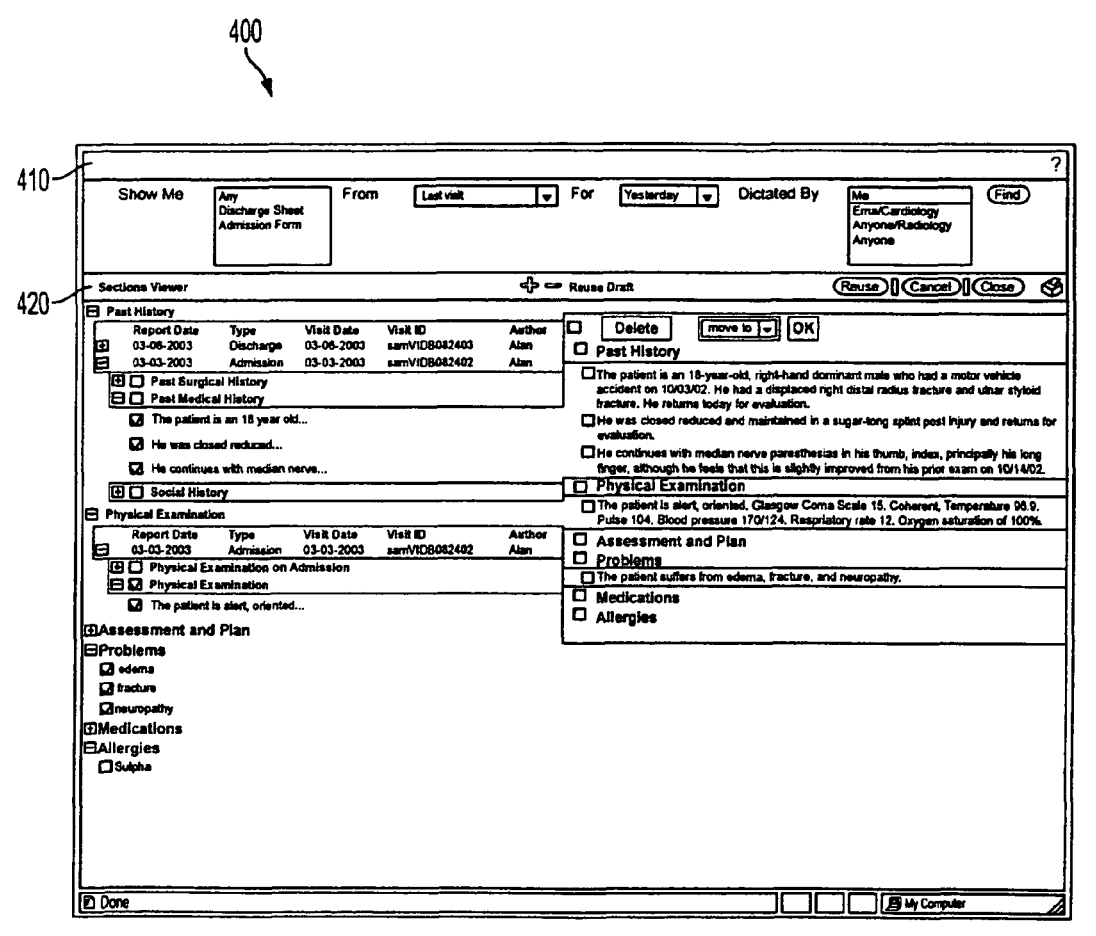

FIG. 4 illustrates a reuse viewer GUI 400 provided by the reuse client module 340 in accordance with yet another embodiment. It should be readily apparent that the elements of the reuse viewer GUI 400 may be deleted and/or modified and new elements added.

Figure 4A:
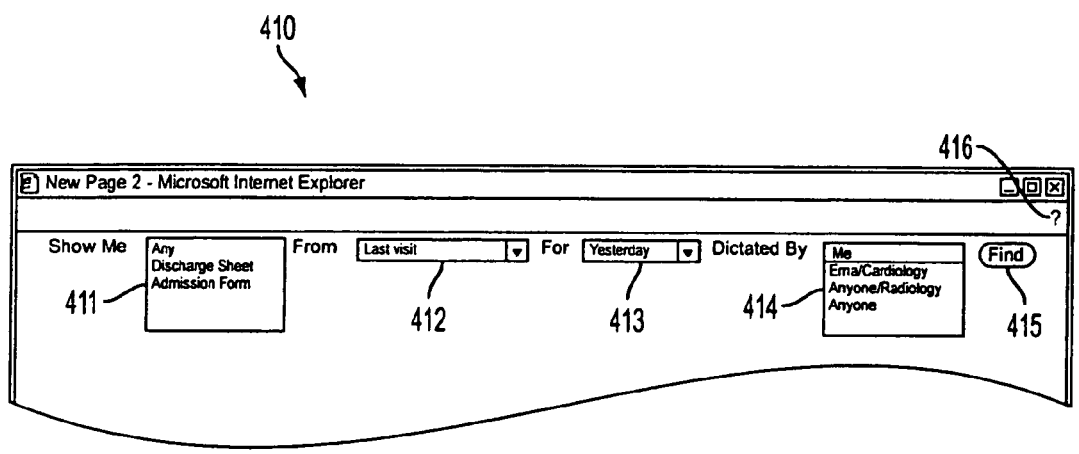
FIG. 4A illustrates a detailed view of the data filter component in accordance with yet another embodiment.

As shown in FIG. 4, the reuse viewer GUI 400 includes a data filter component 410, a section viewer component 420, and a reuse draft viewer 430. The data filter component 410 may be configured to display various query parameters to filter documents. For example, the data filter component 410 may display query options to filter medical records generated by the NLPR system 300 (shown in FIG. 3), which may be shown in greater detail in FIG. 4A.

FIG. 4A illustrates a detailed view of the data filter component 410 in accordance with yet another embodiment. As shown in FIG. 4A for this particular embodiment, the data filter component 410 includes filter (or query) parameters of 'Work-Type' parameter 411, 'Encounter' parameter 412, 'Time Frame' parameter 413, and a 'Dictated By' parameter 414. The work parameter 411 may be configured to have a variety of sub-parameters. For example, the Work Type parameter 411 may include an ~Any" sub-parameter to find all records associated with a selected patient. The sub-parameters of Work Type parameter 411 may also include discharge sheet, admission form, or any other type of record generated for a patient.

The Encounter parameter 412 may be configured to locate the records associated with a type of visit for a patient. In that regard, the Encounter parameter 412 may have sub-parameters of "current visit", "last visit", "current and last visit", and/or "any visit" to assist in the scope of the search for records in the NLPR system 300.

The Time Frame parameter 412 may be configured to locate records within a specified block of time. Accordingly, the Time Frame parameter 412 may include sub-parameters of "yesterday", "last week", and/or "last 30 days" to assist in the scope of the search for records in the NLPR system 300.

The Dictated-By parameter 414 may be configured to locate records authored by a specific user. In that respect, the Dictated-By parameter 414 may include sub-parameters of "me", "anyone", "cardiology", "radiology" or any other department that has contact with a patient, to focus the scope of the search for records in the NLPR system 300.

The reuse viewer GUI 400 also includes a "Find" button 415 and a "Help" button 416. The Find button 415 may be configured to query or apply a data filter to the document database of the NLPR system 300. The results of the search are displayed on the section viewer component 420. The Help button 416 may be configured to display a window of instructions to assist the user in the operation of the reuse viewer GUI 400.

Figure 5:
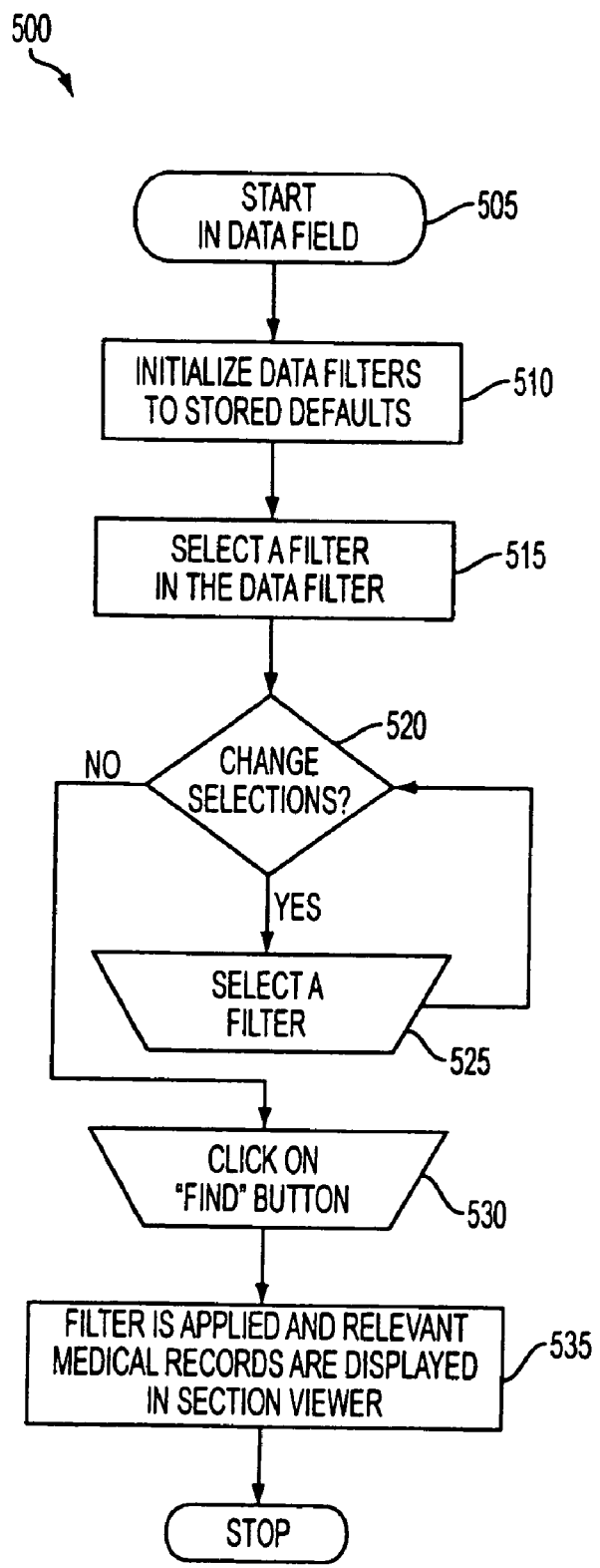
FIG. 5 illustrates a more detailed flow diagram for the data filtering component in accordance with yet another embodiment.

FIG. 5 illustrates a more detailed flow diagram 500 for the data filtering component 410 in accordance with yet another embodiment. It should be readily apparent to those of ordinary skill in the art that this flow diagram 500 represents a generalized illustration and that other steps may be added or existing steps may be removed or modified.

As shown in FIG. 5, the reuse client module 340 may be configured to initiate the data filter component 510, in step 505. More particularly, the reuse client module 340 may determine whether or not a user has specified personal (or customized) filter parameters. If a user has specified the use of customized filter parameters, the reuse client module 340 may be configured to retrieve the customized filter parameters from a predetermined location, e.g., a user profile, and display the customized filter parameters in the data filter component 510. Otherwise, the reuse client module 340 may be configured to display the default filter parameters in the data filter component 510.

In step 515, the reuse client module 340 receives an indication that the user has selected a filter parameter in the data filter component 410. For example, in the default display of the data filter component 410, the reuse client displays 'Work-type' filter, an 'Encounter' filter, a 'Time Frame' filter, and a 'Dictated Persons' filter. In step 520, the reuse client module 340 may determine if user has changed the value in the selected filter. If the user has changed the value, in step 525, the reuse client module 340 may store the parameter and return to step 520. More particularly, the reuse client module 340 may detect a change in the parameters of Work-type, Encounter, Time, and/or Dictated Persons filters. For example, a user may select "Last 30 Days" in the Time filter to query for documents. Otherwise, if the user has not changed the value, the reuse client module 340 may set the filter parameters to a default value, e.g., 'Any' value.

In step 530, the reuse client module 340 may be configured to receive an indication that the user has activated the 'Find' button. Subsequently, the reuse client module 340 may form a query (or filter) the document library with the set filter parameters as discussed above.

In step 535, the reuse client module 340 may be configured to retrieve the relevant documents from the document library and display the relevant documents in the section viewer component 420 of the reuse viewer GUI 400. If documents are not found, the reuse client module 340 may indicate to the user that the query failed to find relevant documents. Subsequently, the reuse client module 340 may be configured to exit the processing for method 500.

Returning to FIG. 4, the section view component 420 may be configured to display the results from a query initiated in the data filter component 410 in a tree-view like structure. The available sections for reuse and its contents are organized as paragraphs in a report-wise format. More particularly, the reuse client module 340 may be configured to organize the documents according to sections. Each document in the NLPR system 300 may be divided into sections. For each section, the reuse client module 340 may be configured to retrieve the associated text from that section in each of the retrieved documents. The retrieved associated text may be then organized as paragraphs under the section in the section viewer component 420, which may be illustrated in FIG. 4B.

Figure 6A:
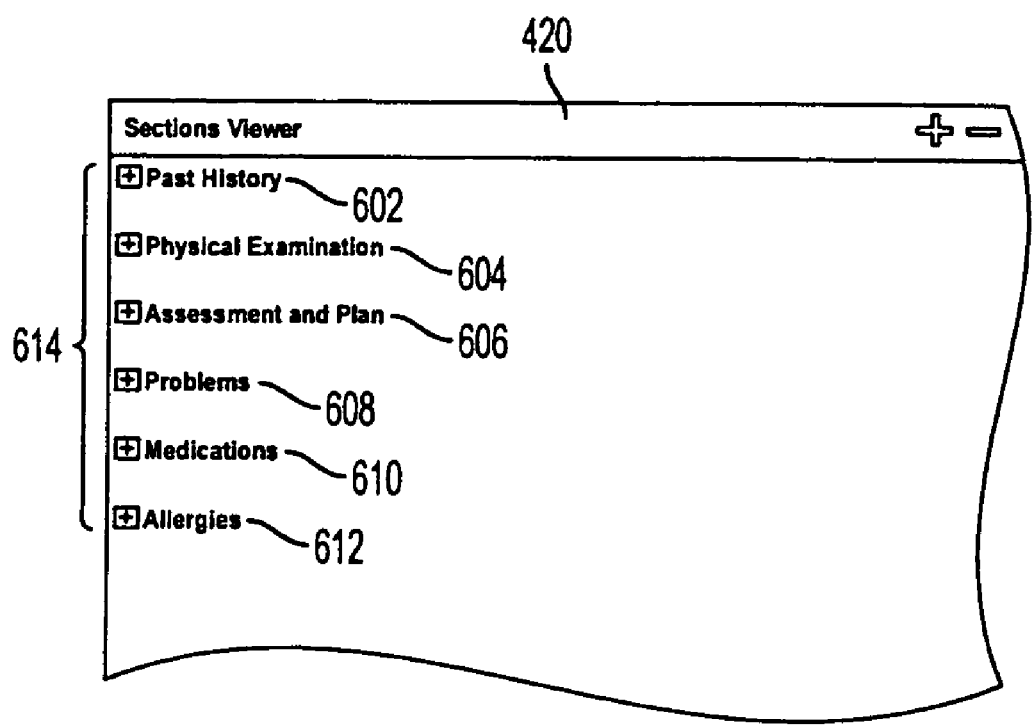
FIG. 6A illustrates a detailed view of the section view component in accordance with yet another embodiment.

FIG. 6A illustrates a detailed view of the section view component 420 in accordance with yet another embodiment. As shown in FIG. 4B, the section view component 420 initially displays sections names (Past History 602, Physical Examination 604, Assessment and Plan 606, Problems 608, Medications 610, and Allergies 612) as a top-level tree. Expand boxes 614 are also display with the associated section name.

Figure 6B:
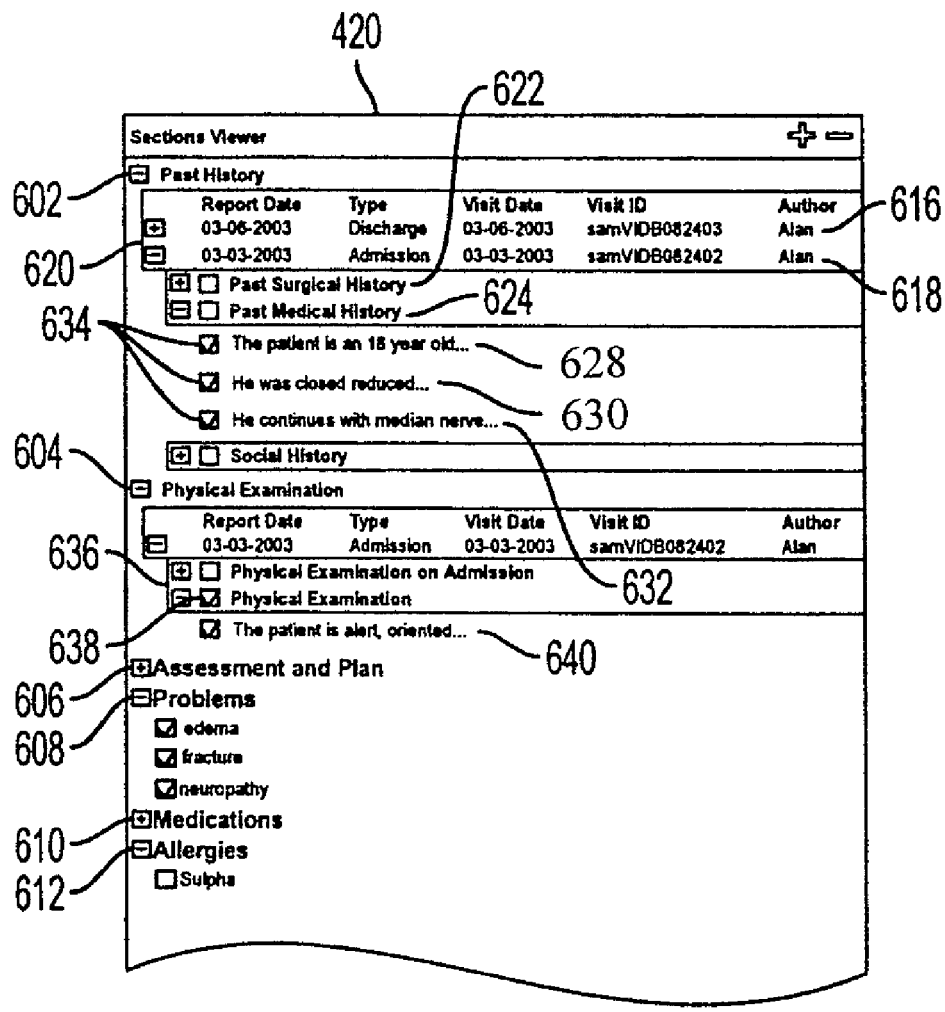
FIG. 6B illustrates a detailed view of the section view component in an expanded view in accordance with yet another embodiment.

When a section may be expanded, i.e., the selected expand box may be activated, the reuse client module 340 may be configured to display a list of reports pertaining to the selected section as the next level item of the tree, where the contents are organized as paragraphs, as illustrated with FIG. 6B.

FIG. 6B illustrates a detailed view of the section view component 420 in an expanded view in accordance with yet another embodiment. As shown in FIG. 4C, the reuse client module 340 may be configured to display the relevant documents found by the data filtering component 410 organized by sections names. More particularly, the section view component 420 displays Past History 602 with two reports 616, 618. The two reports also include associated expand boxes 620.

In this particular view, a user has expanded the view on report 618 to show additional subsections 622, 624. The additional subsections also include associated expand boxes 626. The associated expand box for report 624 was activated to display the individual paragraphs 628, 630, 632. After activation of the expand boxes, the same expand boxes become collapse boxes to collapse the display.

The individual paragraphs 628-632 also include associated check boxes 634. The client reuse module 340 may be configured to append individual paragraphs 628-632 to a draft document in response to the check boxes being activated. The client reuse module may also append sections from a report. For example, Physical Examination 636 under Physical Examination 604 displays associated expand box 626 and associated check box 638. As shown, associated check box 638 may be checked, which then activates the check marks for check boxes 640 of the paragraphs in the subsection Physical Examination 636. The text from the Physical Examination 636 may then be appended to the draft document in response to the activation of check box 638.

Figure 7A:
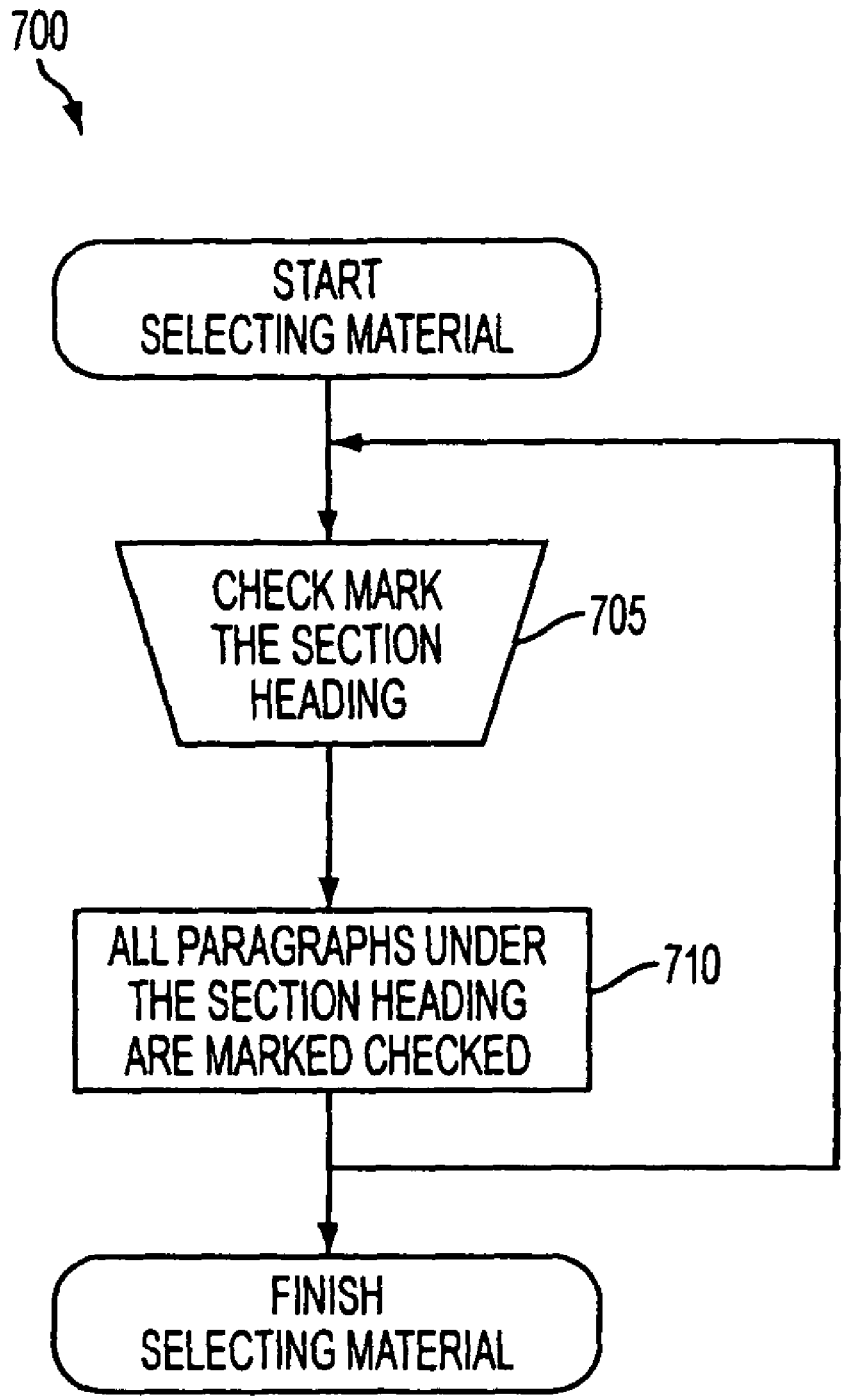
FIG. 7A illustrates a more detailed flow diagram for a section viewer component in accordance with another embodiment.

FIG. 7A illustrates a more detailed flow diagram 700 for section viewer component 420 in accordance with another embodiment. It should be readily apparent to those of ordinary skill in the art that this flow diagram 700 represents a generalized illustration and that other steps may be added or existing steps may be removed or modified.

As shown in FIG. 7A, the reuse client module 340 may receive an indication from the section viewer component 420 that the user has selected a section by activating the selected section, e.g., checking the check box, in step 705.

In step 710, the reuse client module 340 may be configured to select all the paragraphs under the selected section by checking the respective check boxes.

Figure 7B:
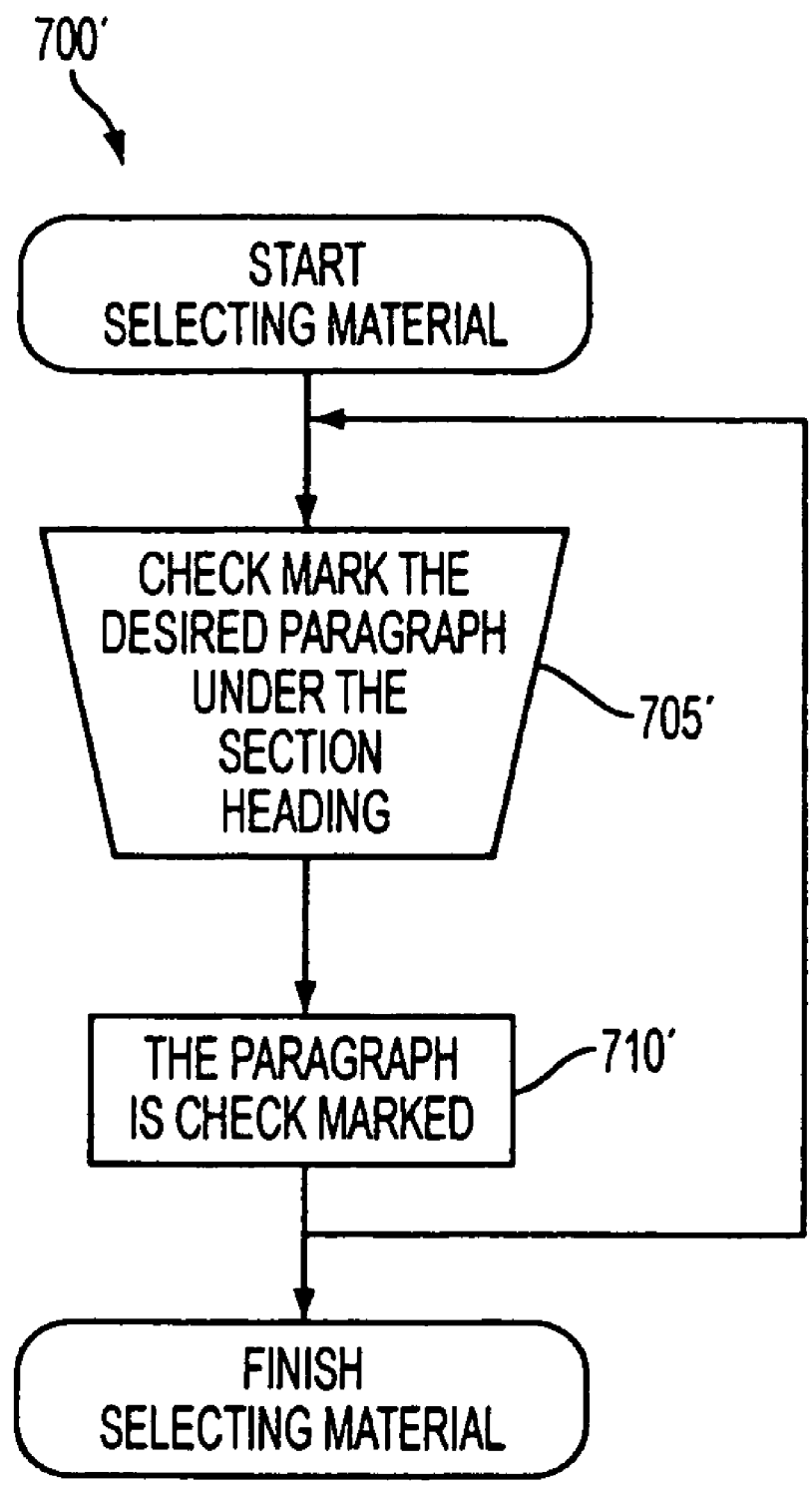
FIG. 7B illustrates a more detailed flow diagram for a section viewer component in accordance with another embodiment.

FIG. 7B illustrates a more detailed flow diagram 700' for section viewer component 420 in accordance with another embodiment. It should be readily apparent to those of ordinary skill in the art that this flow diagram 700' represents a generalized illustration and that other steps may be added or existing steps may be removed or modified.

As shown in FIG. 7B, the reuse client module 340 may be configured to receive indication that a user has selected a section by the expansion of the selected section in step 705'.

In step 710', the reuse client module 340 may be configured to receive indication that the user has selected a paragraph(s) with the selected section by the checking of the selected paragraph(s).

Returning to FIG. 4, the reuse draft component 430 may be configured to provide an at-a-glance view of all paragraphs and/or sections selected from the section view component 420 in a draft (or current) document. The reuse draft component 430 may also provide a user the capability to reuse paragraphs from one section in another section of a current report. An example of the reuse draft component 430 in conjunction with the section view component 420 may be illustrated in FIG. 8 in accordance with yet another embodiment.

Figure 8:
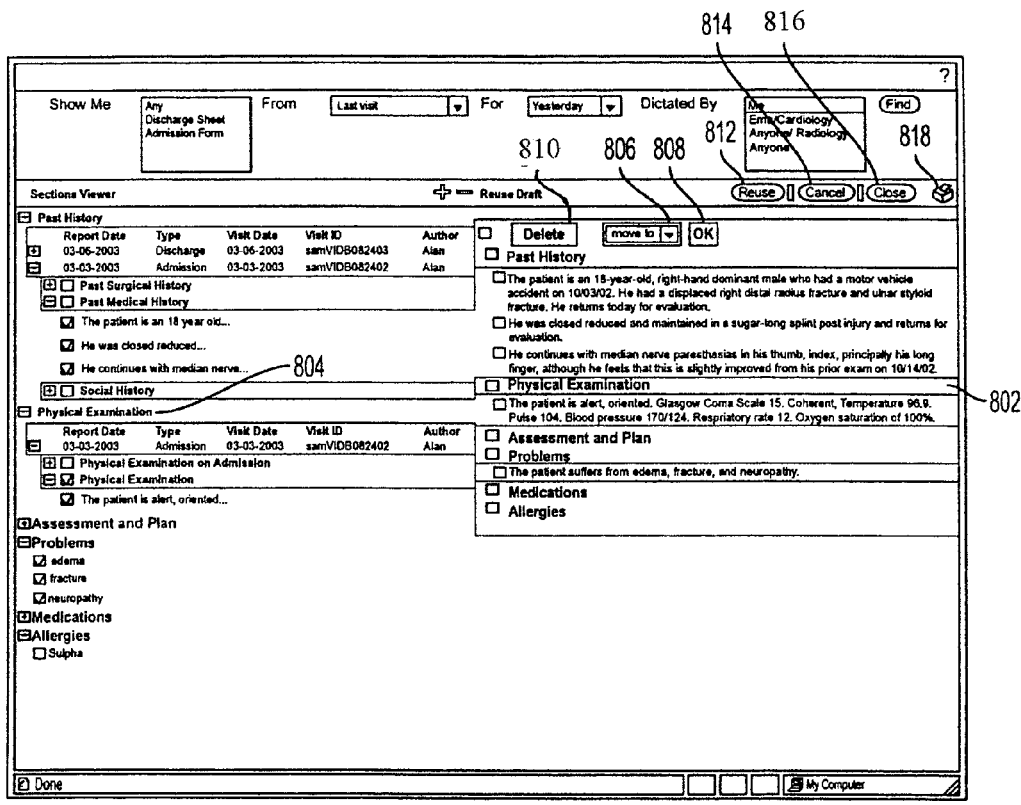
FIG. 8 illustrates an exemplary display of the reuse draft component in conjunction with the section view component in accordance with yet another embodiment.

As shown in FIG. 8, the reuse client module 340 may be configured to highlight a Physical Examination section 802 when a user hovers over the Physical Examination section 802 with a cursor. The reuse client module 340 may display the paragraphs from the Physical Examination section 804 in the section viewer component 420. The reuse client module 340 may also be configured to append selected paragraphs to the current document displayed on the reuse draft component 430 in response to a selection of the selected paragraphs in the section viewer component 420.

The reuse draft component 430 also includes a 'Move-to' drop down box 806, an 'OK' button 808, a 'Delete' button 810, a 'Reuse' button 812, a 'Cancel' button 814, a 'Close' button 816, and a 'Print' icon 818. The Move-to drop down box 806 may be configured to move a highlighted paragraph to another section within the reuse draft component 430. More particularly, a user may activate the associated check box(es) for selected section(s). The user then selects a destination section in the Move-to drop down box 806. Subsequently, the user activates the OK button 808, which then removes the selected paragraphs from 808 and which may be configured to initiate the transfer from a source section to a destination section for the Move-to function.

The Delete button 810 may be configured to erase or remove highlighted paragraphs from the current document in the reuse draft component 430. More specifically, a user may activate the associated check box(es) for selected paragraph(s). The user then activates the Delete button 810 to delete the selected paragraph(s).

The Reuse button 812 may be configured to copy selected material to the host application. More particularly, the reuse client module 340 may copy the contents of the current document to the host application in response to the activation of the Reuse button 812. Subsequently, the reuse viewer GUI interface 400 closes and control returns the host application.

The Cancel button 814 may be configured not to implement any of the changes to a current document in the reuse draft component 430. More particularly, the reuse client 430 may clear the paragraph(s) copied to the reuse draft component 430 and return to the host application.

The Close button 450 may be configured to close the reuse viewer GUI 400. More specifically, the reuse client 340 may display a dialog window to advise a user that closing the reuse viewer GUT 400 will result in losing the current copied data. If the user selects to close the window, the reuse client module 340 initiates an exiting routine for the reuse viewer GUI 400. Otherwise, if the user decides not to cancel, the reuse client module 340 returns to the reuse viewer GUI 400.

Figure 9:
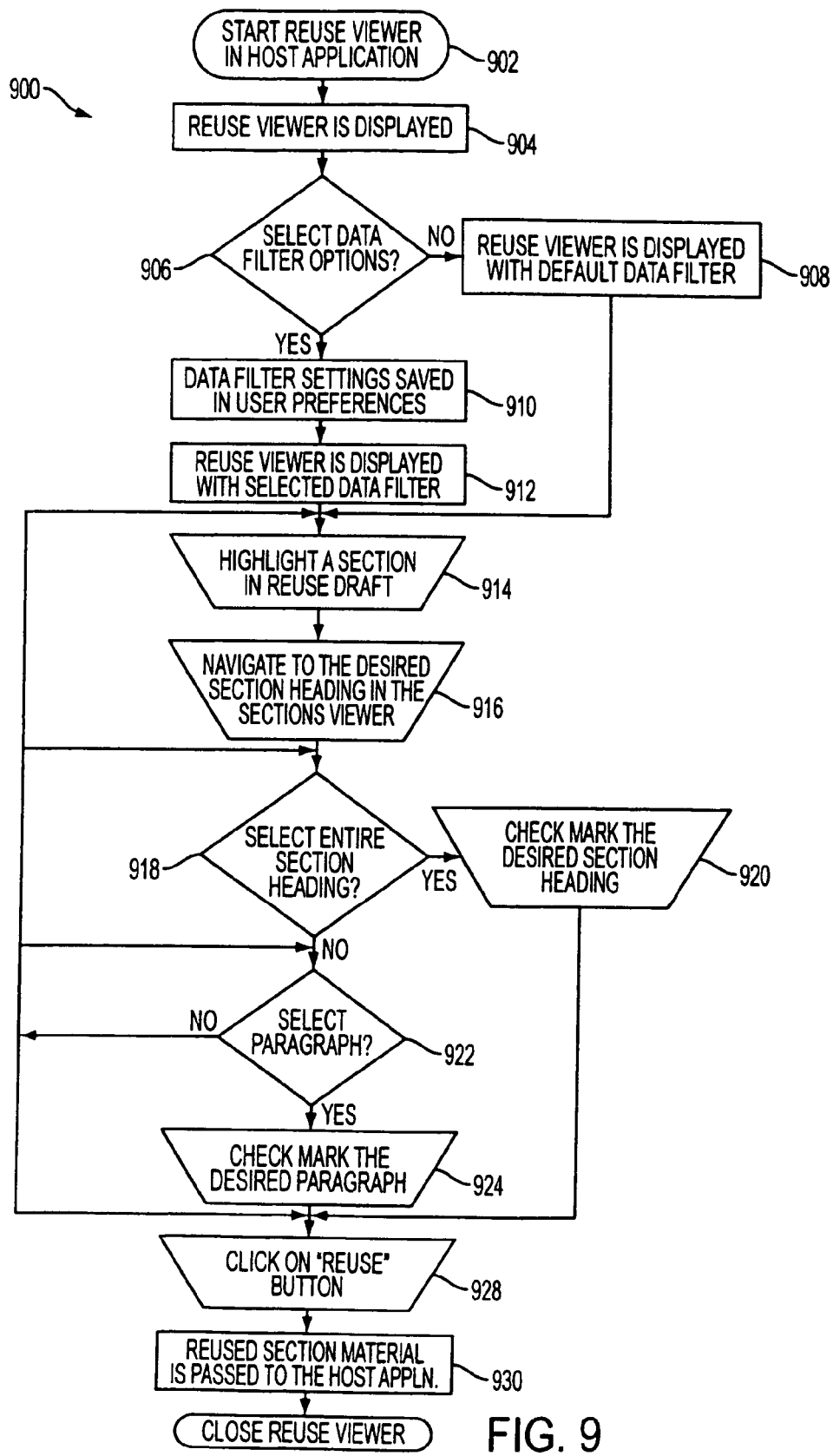
FIG. 9 illustrates a flow diagram of the reuse client module shown in FIG. 3 in accordance with yet another embodiment.

FIG. 9 illustrates a flow diagram 900 of the reuse client module 340 in accordance with yet another embodiment. It should be readily apparent to those of ordinary skill in the art that this flow diagram 900 represents a generalized illustration and that other steps may be added or existing steps may be removed or modified.

As shown in FIG. 9, the reuse client module 340 may be initiated by a host application, e.g., NLPR system 300, in step 902. More particularly, the host application may invoke the reuse client module by activating a menu item, an icon, command line prompt or other similar program initiation technique. The host application may specify attributes in the initiation of the reuse client module 340. For example, the NLPR system 300 specifies the attributes of provider, patient, dictated persons, and the sections to reuse. As another example, for a patent attorney system, the host application may specify the attributes of the client, dictated persons, and sections to reuse.

In step 904, the client reuse module 330 may display the graphical user interface such as the reuse viewer GUI 400.

In step 906, in displaying the data filter component 410, the reuse client module 340 may prompt a user of whether or not to select customized filter (or query) parameters that have been previously saved in a user preference profile, if the user decides not to use the customized filter parameters, the reuse client module 340 may display default filter parameters, e.g., parameters shown in FIG. 4A, in step 908. Otherwise, in step 910, the reuse client module 340 may retrieve the customized filter parameters from the user preference profile. In step 912, the reuse client module 340 may display the customized filter parameters on the data filter component 410. Subsequently, the reuse client module 340 may display the data filter component 410 with the appropriate data filter parameters, the section viewer component 420, and the reuse draft component 430.

In step 914, a user may highlight a section displayed on the reuse draft component 430. The reuse client module 340 may be configured to display the sections where reuse may be possible and in the order that the sections appear in the host application, in step 916.

In step 918, the reuse client module 340 may be configured to determine whether a user selected an entire section or selected paragraphs in response to a user activation of a section heading. If the user selected the entire section heading, the reuse client module 340 may mark the entire section as being used, in step 920. Otherwise, the reuse client module 340 determines whether or not an individual paragraph under the section heading has been selected, in step 922.

if the reuse client module 340 determines that a paragraph has not been selected, the reuse client returns to the processing of step 918. Otherwise, the reuse client module 340 may mark the selected paragraphs as check in the section view component 420, in step 922.

In step 924, the reuse client module may be configured to append the material with check marks to the current document displayed in the reuse draft component 430. Subsequently, the reuse client module 340 may prompt a user through a dialog box whether or not the user would like to modify the filter settings. If the reuse client module 340 receives indication that the user would like to modify the filter settings, the reuse client module 340 may filter for new documents in the document library of the NLPR system 300. The reuse client module 340 may display the newly filtered documents in the section viewer component 420 with appropriate markings for sections that have already been reused.

In step 928, when the reuse client module 340 receives indication that the Reuse button 446 has been activated, the reuse client module 340 may transfer the contents of the reuse draft section to the calling host application. e.g., the NLPR system 300. Subsequently, in step 930, the reuse client module 340 closes the reuse viewer GUI 400.

Figure 10:
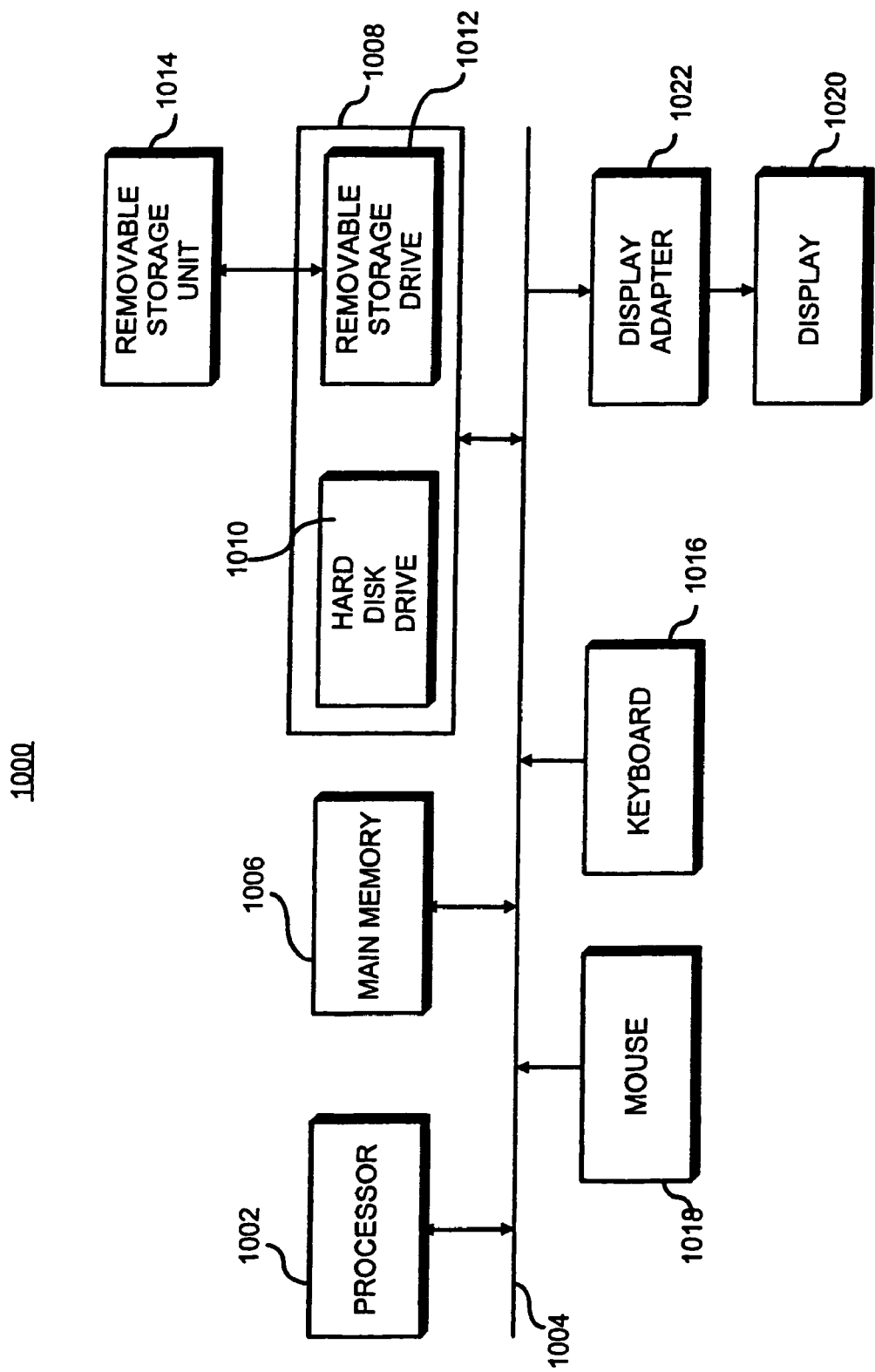
FIG. 10 illustrates an exemplary block diagram of a computer system where an embodiment may be practiced.

FIG. 10 illustrates an exemplary block diagram of a computer system 1000 where an embodiment may be practiced. The functions of the expressway routing module may be implemented in program code and executed by the computer system 1000. The reuse client module 340 and the NLPR system 300 may be implemented in computer languages such as PASCAL, C, C++, JAVA, etc.

As shown in FIG. 10, the computer system 1000 includes one or more processors, such as processor 1002, that provide an execution platform for embodiments of the expressway routing module. Commands and data from the processor 1002 are communicated over a communication bus 1004. The computer system 1000 also includes a main memory 1006, such as a Random Access Memory (RAM), where the software for the expressway routing module may be executed during runtime, and a secondary memory 1008. The secondary memory 1008 includes, for example, a hard disk drive 1010 and/or a removable storage drive 1012, representing a floppy diskette drive, a magnetic tape drive, a compact disk drive, etc., where a copy of a computer program embodiment for the expressway routing module may be stored. The removable storage drive 1012 reads from and/or writes to a removable storage unit 1014 in a well-known manner. A user interfaces with the expressway routing module with a keyboard 1016, a mouse 1018, and a display 1020. The display adaptor 1022 interfaces with the communication bus 1004 and the display 1020 and receives display data from the processor 1002 and converts the display data into display commands for the display 1020.

Certain embodiments may be performed as a computer program. The computer program may exist in a variety of forms both active and inactive. For example, the computer program can exist as software program(s) comprised of program instructions in source code, object code, executable code or other formats; firmware program(s); or hardware description language (HDL) files. Any of the above can be embodied on a computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present invention can be configured to access, including signals downloaded through the Internet or other networks. Concrete examples of the foregoing include distribution of executable software program(s) of the computer program on a CD-ROM or via Internet download. In a sense, the Internet itself, as an abstract entity, may be a computer readable medium. The same may be true of computer networks in general.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Those skilled in the art will recognize that these and other variations are possible within the spirit and scope as defined in the following claims and their equivalents.

FIG. 10 illustrates a more detailed flow diagram 900 for reuse draft component 430 in accordance with another embodiment. It should be readily apparent to those of ordinary skill in the art that this flow diagram 800 represents a generalized illustration and that other steps may be added or existing steps may be removed or modified.

As shown in FIG. 8, the reuse client module 340 may be configured to receive indication that the user chooses to add material to a current document in the reuse draft component 430 by hovering over a selected section, in step 805. Subsequently, the reuse client module 340 may highlight the selected section, in step 810.

In step 815, the reuse client module 340 may receive indication that the user has expanded the associated selected section in the section viewer component 420. In step 820, the reuse client module 340 may receive a selection of individual paragraph(s) or entire selection for reuse by the user selecting the appropriate check box, as discussed above.

In step 820, the reuse client module 340 may append the selected material from step 820 to the current document in the reuse draft component 430. Subsequently, the reuse client module 340 enters an idle state waiting for user input.

For the convenience of the reader, the above description has focused on a representative sample of all possible embodiments, a sample that teaches the principles of the invention and conveys the best mode contemplated for carrying it out. The description has not attempted to exhaustively enumerate all possible variations. Further undescribed alternative embodiments are possible. It will be appreciated that many of those undescribed embodiments are within the literal scope of the following claims, and others are equivalent.

What is claimed is:

1. A computer-implemented method of providing a graphical user interface (GUI), using a processor, that facilitates reusing information from one or more previous electronic documents in a new electronic document, the method comprising:

displaying a query interface having at least one data filter component that presents a plurality of query parameters;

receiving, via the query interface, at least one selected query parameter;

querying a database of computer electronic documents with the at least one selected query parameter;

grouping results of querying the database for display into a plurality of captioned sections, each of the plurality of captioned sections containing content from the electronic documents associated with the respective captioned section;

displaying the results of querying the database in a section viewer component, the section viewer component displaying the results in a tree structure comprising:

a section level component for displaying each of the plurality of captioned sections in association with a respective expand/collapse graphical component, each expand/collapse graphical component having a display state that is either in a collapsed state or an expanded state such that, when actuated, the section level component displays or hides content under the respective captioned section in accordance with the display state of the respective expand/collapse graphical component; and a content level component that selectively displays one or more contents associated with each of the plurality of captioned sections in accordance with whether the respective expand/collapse graphical component is in the collapsed state or the expanded state, each of the one or more contents having an associated selection graphical component displayed therewith, each of the one or more displayed selection graphical components comprising information indicating whether it is m a selected state or a non-selected state;

in response to receiving input from a user via any one of the one or more displayed selection graphical components altering the state of that displayed selection graphical component; and in response to receiving an input from the user via the graphical user interface indicating that the user has finished altering the states of the one or more displayed selection graphical components copying each of the contents having an associated selection graphical component that is in the selected state into the new electronic document.

2. The method of claim 1, further comprising:
upon receiving the indication from the user via the graphical user interface, refraining from copying each of the contents that does not have an associated selection graphical component selected into the new electronic document.

3. The method of claim 2, wherein each of the previous electronic documents comprises a medical record.

4. The method of claim 3, wherein the new electronic document comprises a medical record.

5. The method of claim 2, wherein the new electronic document comprises a medical record.

6. The method of claim 1, wherein each of the previous electronic documents comprises a medical record.

7. The method of claim 6, wherein the new electronic document comprises a medical record.

8. The method of claim 1, wherein the new electronic document comprises a medical record.

* * * * *